United States Patent
Zagorii

(10) Patent No.: US 9,795,609 B2
(45) Date of Patent: Oct. 24, 2017

(54) PHARMACEUTICAL COMPOSITION OF 1-ADAMANTYLETHYLOXY-3-MORPHOLINO-2-PROPANOL OR PHARMACEUTICALLY ACCEPTABLE SALTS THEREOF FOR THE TREATMENT OF CARDIOVASCULAR DISEASE

(71) Applicant: Gleb Vladimirovich Zagorii, Kiev (UA)

(72) Inventor: Gleb Vladimirovich Zagorii, Kiev (UA)

( * ) Notice: Subject to any disclaimer, the term of this patent is extended or adjusted under 35 U.S.C. 154(b) by 52 days.

(21) Appl. No.: 14/433,419

(22) PCT Filed: Sep. 17, 2013

(86) PCT No.: PCT/UA2013/000105
§ 371 (c)(1),
(2) Date: Apr. 3, 2015

(87) PCT Pub. No.: WO2014/055053
PCT Pub. Date: Apr. 10, 2014

(65) Prior Publication Data
US 2015/0246051 A1    Sep. 3, 2015

(30) Foreign Application Priority Data

Oct. 5, 2012  (UA) .................................. 201211510
Sep. 9, 2013  (UA) .................................. 201310845

(51) Int. Cl.
*A61K 31/5375*    (2006.01)
*A61K 9/00*    (2006.01)

(52) U.S. Cl.
CPC ........ *A61K 31/5375* (2013.01); *A61K 9/0019* (2013.01)

(58) Field of Classification Search
CPC .................................................. A61K 31/5375
See application file for complete search history.

(56) References Cited

U.S. PATENT DOCUMENTS 3,705,213 A *  12/1972  Pfeiffer et al. ................ 558/169
6,492,355 B1  12/2002  Alcaraz et al.

FOREIGN PATENT DOCUMENTS

RU    2254333 C2    6/2005
UA      53558 A    1/2003

OTHER PUBLICATIONS

Prytula, T. P.; Pupysheva, O. V.; Korotky, Yu. V.; Mokhort, M. A.; Lozinsky, M. O. Zhurnal Organichnoi to Farmatsevtichnoi Khimii (2010), 8(1), 25-29. (Abstract and Entire Document in Ukranian).*
Boudina et al., Diabetic Cariomyopathy Revisited, Circulation. 2007:115:3213-3223.*
Pritula, et al. Ukranian Medicine, PTO 103351 English translation of Pritula et al., Journal of Organic and Pharmacological chemistry, vol. 8, Issue No. 29, 2010, p. 25-29.*
Ademol-Darnitsa, Normativno-direktivnye dokumenty MOZ Ukrainy, Nomer registratsionnogo udostovereniia: UA/4845/01/01 on Jul. 26, 2006, retrieved from the Internet <URL:http://mozdocs.kiev.ua/likiview.php?id=5132> on Mar. 16, 2015.
International Searching Authority, International Search Report for International Application No. PCT/UA2013/000105, dated Dec. 26, 2013, 9 pages, Federal Service for Intellectual Property, Russia.
Masri, Carolina, et al., "Apoptosis: a potentially reversible, metastable state of the heart", Heart Failure Review, 2008, vol. 13, pp. 175-179, Springer, U.S.A.
Mochort, M.A., "Comparative Spasmolytic Activity Drotaverine, Pinacidil and Its Fluorinated Analog Flocalin" *Achieving Biology Medicine*, 2001, No. 1, vol. 17, pp. 4-6, UDC 615.015.13;615.217. 5;615.015.23, Ukraine.

* cited by examiner

*Primary Examiner* — San-Ming Hui
(74) *Attorney, Agent, or Firm* — Alston & Bird LLP

(57) ABSTRACT

A pharmaceutical composition for parenteral administration containing the active ingredient 1-adamantylethyloxy-3-morpholino-2-propanol, or pharmaceutically acceptable salts thereof, in a concentration range of from 3 to 100 mg/ml for the treatment of cardiovascular disease.

5 Claims, No Drawings

PHARMACEUTICAL COMPOSITION OF 1-ADAMANTYLETHYLOXY-3-MORPHOLINO-2-PROPANOL OR PHARMACEUTICALLY ACCEPTABLE SALTS THEREOF FOR THE TREATMENT OF CARDIOVASCULAR DISEASE

This application is a national stage application, filed under 35 U.S.C. §371, of International Application No. PCT/UA2013/000105, filed Sep. 17, 2013, which claims priority to Ukrainian Application No. 2012 11510, filed Oct. 5, 2012, and Ukrainian Application No. 2013 10845, filed Sep. 9, 2013, the contents of all of which as are being hereby incorporated by reference in their entirety.

The invention relates to medicine and pharmacy and concerns a pharmaceutical composition for parenteral use comprising the active substance 1-adamantylethyloxy-3-morpholino-2-propanol or pharmaceutically acceptable salts thereof within the concentration range of 3-100 mg/ml for treatment of cardiovascular pathology.

It is recognized that main pathogenetic segments effecting on coronary artery disease development is the use of drugs that restore or improve myocardial perfusion and reduce its need in oxygen (nitrates, β-adrenoreceptor blockers). In case of myocardial infarction (therapeutic window to 3 hours) the mechanical revascularization and thrombolytic therapy enable to prevent the development of myocardial necrosis and significantly improve mortality indices and quality of life of these patients. Unfortunately, it is not possible to treat most of patients with this methods for various reasons including: 1) late diagnosis and falling outside the therapeutic window; 2) availability of contraindications etc. In this regard, there is a problem for development of other alternative methods aimed at protecting cardiomyocytes from ischemic factor action. One of the possible solutions of this problem is to use drugs with cardioprotective properties in schemes of intensive therapy.

Despite significant advances in making new drugs with specified action (metabolite tropic cardioprotectors) the effectiveness of majority of them from the view of evidence-based medicine is not established, but the drugs in this class having undoubted in scientists and clinicians positive effect on ischemic myocardium (trimetazidine) are indicated for the prevention of strokes in the recovery period at myocardial infarction and cardiomyopathy only (see Compendium 2005, p. 295, Morion). That is, their effect is demonstrated mainly in long-term hypoxic myocardial injury.

The separate nosology group causing morphological changes of cardiomyocytes is the cardiomyopathies of various genesis including postinfarction, metabolic, and as a result of chronic exogenous or endogenous intoxication, particularly on the background of intake of alcohol or cardiotoxic drugs (antituberculous, cytostatics) etc.

The basis for the development of a pharmaceutical composition for parenteral use comprising the active substance 1-adamantylethyloxy-3-morfolino-2-propanol or pharmaceutically acceptable salts thereof, is that they are able to block the development of ischemic cascade in myocardium at the initial stages of its formation, and have antihypoxic, antioxidant properties, corrective action on energy metabolism and acid-alkali status in cardiomyocytes. The result of this cardioprotection is the preservation of morphological myocardial organization. Since the hypoxia is a typical pathophysiological process, which is a key element in all forms of ischemic heart disease and cardiomyopathy, it makes the use of proposed composition perspective as a drug, both in acute myocardial ischemia and at long-term coronary insufficiency and cardiomyopathies.

The object of claimed invention is the making of a pharmaceutical composition for parenteral use comprising the active substance 1-adamantylethyloxy-3-morpholino-2-propanol or pharmaceutically acceptable salts thereof for pharmacotherapy of cardiovascular pathology of various geneses.

The proposed pharmaceutical composition can be used to treat cardiovascular diseases, namely various forms of coronary artery disease, including unstable angina pectoris, stable rest and extertional angina pectoris, angina pectoris of intact vessels, acute coronary syndrome (including early postinfarction angina pectoris), myocardial infarction (large-focal and small-focal, repeated and recurrent), post resuscitation disease (state after emergency procedures), treatment and prevention of ischemic myocardial postreperfusion injuries after thrombolysis, stenting, balloon angioplasty, coronary vessels atheroctomy, postinfarction myocardiosclerosis, cardiomyopathies of various genesis (alcoholic, infectious-toxic, and metabolic), heart rhythm disorders, diabetic angiopathies and complications thereof due to the ability to block the development of ischemic cascade in myocardium at the initial stages of its formation as well as anti-hypoxic, antioxidant properties, corrective effect on energy metabolism and acid-alkali status in cardiomyocytes.

EXAMPLE 1

Experiments in cats found that the use of the pharmaceutical composition for parenteral use comprising the active substance 1-adamantylethyloxy-3-morpholino-2-propanol or pharmaceutically acceptable salts thereof at doses 3; 5; and 10 mg/kg intravenously stimulates coronary blood flow. Moreover, said action is not associated with peripheral vasodilatation, decreased of venous inflow and cardiac output and not accompanied by hypotension. The ability of the pharmaceutical composition for parenteral use comprising the active substance 1-adamantylethyloxy-3-morpholino-2-propanol or pharmaceutically acceptable salts thereof to improve myocardial perfusion indicates to appropriateness of its use in acute coronary syndrome.

EXAMPLE 2

Experimental therapy of rats with small-focus myocardial infarction with the pharmaceutical composition for parenteral use comprising the active substance 1-adamantylethyloxy-3-morpholino-2-propanol or pharmaceutically acceptable salts thereof at a dose of 10 mg/kg once a day for 96 hours of ischemia promoted the increasing of c-fos protein content in cardiomyocytes, resulting in decreased intensity of its necrosis in ischemic focus cells. At that, the percentage of necrotic cardiomyocytes is reduced by switching morphological type of cell death from necrotic to "softer" apoptotic one. The ability of the pharmaceutical composition for parenteral use comprising the active substance consisting 1-adamantylethyloxy-3-morpholino-2-propanol or pharmaceutically acceptable salts thereof to inhibit cardiomyocyte necrosis demonstrates the appropriateness of its use in myocardial infarction.

EXAMPLE 3

Experimental treatment of rats with small-focus myocardial infarction with the pharmaceutical composition for parenteral use comprising the active substance 1-adamantylethyloxy-3-morpholino-2-propanol 10 mg/kg once a day for 96 hours promoted the increasing of bcl-2 antiapoptotic protein expression which provided the inhibition of apoptosis and maintained the morphofunctional activity of perifocal cardiomyocytes and in those myocardial areas where the restoration of blood flow occurred (spontaneous reperfusion and opening of collaterals). The ability of the pharmaceutical composition for parenteral use comprising the active substance 1-adamantylethyloxy-3-morfolino-2-propanol or pharmaceutically acceptable salts thereof demonstrates the appropriateness of its use for the treatment and prevention of ischemic postreperfusion myocardial injuries after thrombolysis, stenting, balloon angioplasty, and coronary vessels atheroctomy.

EXAMPLE 4

Therapeutic administration to rats with small-focus myocardial infarction of the pharmaceutical composition for parenteral use comprising the active substance 1-adamantylethyloxy-3-morpholino-2-propanol or pharmaceutically acceptable salts thereof at a dose of 10 mg/kg once a day for 96 hours of ischemia, accompanied by retention of cardiomyocytes nuclei density on the background of decreasing their area by the prevalence of binuclear cells, increasing of RNA content and transcriptional activity. The ability of the pharmaceutical composition for parenteral use comprising the active substance 1-adamantylethyloxy-3-morpholino-2-propanol or pharmaceutically acceptable salts thereof allows its use for treatment of cardiomyopathies of various geneses (alcoholic, infectious, toxic, and metabolic).

EXAMPLE 5

Therapeutic administration to rats with small-focus myocardial infarction of the pharmaceutical composition for parenteral use comprising the active substance 1-adamantylethyloxy-3-morpholino-2-propanol or pharmaceutically acceptable salts thereof at a dose of 3; 10; 20; 50 and 100 mg/kg once a day for 96 hours of ischemia promoted to reduce manifestations of endothelial dysfunction and nitrosating stress. This allows to use it for treatment of various forms of coronary artery disease, including unstable angina pectoris, stable rest and exertional angina pectoris, angina pectoris of intact vessels, acute coronary syndrome (including early postinfarction angina pectoris), myocardial infarction (large-focus and small-focus, repeated and recurrent) post resuscitation disease (state after emergency procedures), treatment and prevention of ischemic myocardial postreperfusion injuries after thrombolysis, stenting, balloon angioplasty, coronary vessels atheroctomy, postinfarction myocardiosclerosis, cardiomyopathies of various genesis (alcoholic, infectious-toxic, and metabolic), heart rhythm disorders, diabetic angiopathies and complications thereof.

EXAMPLE 6

Preventive single administration to rats of the pharmaceutical composition for parenteral use comprising the active substance 1-adamantylethyloxy-3-morpholino-2-propanol or pharmaceutically acceptable salts thereof at doses of 15; 30; 50 and 100 mg/kg, which is used one hour before the acute adrenal cardiomyopathy simulation, promoted the reducing mortality in rats. This allows to use it for treatment of various forms of ischemic heart disease, including unstable angina pectoris, stable rest and exertional angina pectoris, angina pectoris of intact vessels, acute coronary syndrome (including early postinfarction angina pectoris), myocardial infarction (large-focus and small-focus, repeated and recurrent) post resuscitation disease (state after emergency procedures), and cardiomyopathies of various genesis (alcoholic, infectious-toxic, and metabolic).

Thus, the results of the studies demonstrate that the active substance and pharmaceutical composition for parenteral use comprising the active substance 1-adamantylethyloxy-3-morpholino-2-propanol or pharmaceutically acceptable salts thereof within the concentration range of 3-100 mg/ml have expressed therapeutic properties for various models of cardiovascular pathology. This gives grounds to expect their effectiveness under clinical conditions in treatment of ischemic heart disease including unstable angina pectoris, stable rest and exertional angina pectoris, angina pectoris of intact vessels, acute coronary syndrome (including early postinfarction angina pectoris), myocardial infarction (large-focus and small-focus, repeated and recurrent), post resuscitation disease (state after emergency procedures), treatment and prevention of ischemic myocardial postreperfusion injuries after thrombolysis, stenting, balloon angioplasty, coronary vessels atheroctomy, postinfarction myocardiosclerosis, cardiomyopathies of various genesis (alcoholic, infectious-toxic, and metabolic), heart rhythm disorders, diabetic angiopathies and complications thereof.

The invention claimed is:

1. A method of treating ischemic heart disease comprising administering a pharmaceutical composition comprising about 3-100 mg/ml of 1-adamantylethyloxy-3-morpholino-2-propanol or pharmaceutically acceptable salts thereof to a patient by parenteral administration such that the pharmaceutical composition blocks ischemic cascade development in myocardium, wherein the patient is suffering from one or more of unstable angina pectoris, stable rest and exertional angina pectoris, angina pectoris of intact vessels, acute coronary syndrome, myocardial infarction, post resuscitation disease, ischemic myocardial postreperfusion injuries after thrombolysis, stenting, balloon angioplasty, coronary vessels atheroctomy, postinfarction myocardiosclerosis, cardiomyopathies of various genesis, heart rhythm disorders, diabetic angiopathies and complications thereof.

2. The method of treating ischemic heart disease of claim 1, wherein the acute coronary syndrome is early postinfarction angina pectoris.

3. The method of treating ischemic heart disease of claim 1, wherein the myocardial infarction is one of large-focus or small-focus myocardial infarction.

4. The method of treating ischemic heart disease of claim 1, wherein the myocardial infarction is one of repeated or recurrent myocardial infarction.

5. The method of treating ischemic heart disease of claim 1, wherein the cardiomyopathies is one of alcoholic, infectious-toxic, or metabolic cardiomyopathies.

* * * * *